(12) United States Patent
Martin et al.

(10) Patent No.: US 8,586,702 B2
(45) Date of Patent: Nov. 19, 2013

(54) SUBSTITUTED 3,4-PROPYLENEDIOXYTHIOPHENE MONOMERS AND 3,4-PROPYLENEDIOXYTHIOPHENE-BASED CROSSLINKERS AND POLYMERS THEREOF

(75) Inventors: David C. Martin, Lincoln University, PA (US); Kathleen E. Feldman, Wilmington, DE (US)

(73) Assignee: University of Delaware, Newark, DE (US)

( * ) Notice: Subject to any disclaimer, the term of this patent is extended or adjusted under 35 U.S.C. 154(b) by 81 days.

(21) Appl. No.: 13/215,321

(22) Filed: Aug. 23, 2011

(65) Prior Publication Data

US 2012/0178893 A1 Jul. 12, 2012

Related U.S. Application Data

(60) Provisional application No. 61/377,694, filed on Aug. 27, 2010.

(51) Int. Cl.
 *C08G 75/00* (2006.01)
(52) U.S. Cl.
 USPC ............. 528/377; 528/380; 528/30; 528/373; 549/4; 549/50; 536/18.1
(58) Field of Classification Search
 USPC .................. 528/377, 380, 373, 30; 549/50, 4; 536/18.1
 See application file for complete search history.

(56) References Cited

U.S. PATENT DOCUMENTS

| 2002/0196518 | A1 | 12/2002 | Xu et al. |
| 2004/0072987 | A1 | 4/2004 | Groenendaal |
| 2005/0157369 | A1 | 7/2005 | Xu et al. |
| 2005/0246888 | A1 | 11/2005 | Reynolds et al. |
| 2009/0221763 | A1* | 9/2009 | Reynolds et al. ............. 525/419 |

FOREIGN PATENT DOCUMENTS

WO 2006117800 A2 11/2006

OTHER PUBLICATIONS

International Search Report dated Mar. 26, 2012, PCT/US2011/048780.
Ng, S. C. et al., "Synthesis and characterization of electrically conducting copolymers of ethylenedioxythiophene and 1,3-propylenedioxythiophene with w-functional substituents," Journal of Materials Science Letters 1997, 16, 809-811.
Roncali, J. et al., "3,4-Ethylenedioxythiophene (EDOT) as a versatile building block for advanced functional pi-conjugated systems," J. Mater. Chem. 2005, 15, 1589-1610.
Sinha, J. et al., "Processable, Regioregular, and "Click"able Monomer and Polymers Based on 3,4-Propylenedioxythiophene with Tunable Solubility," Macromolecules 2009, 42, 2015-2022.

* cited by examiner

*Primary Examiner* — Shane Fang
(74) *Attorney, Agent, or Firm* — RatnerPrestia

(57) ABSTRACT

Substituted 3,4-propylenedioxythiophene monomers may be prepared by reacting 3-allyl-3,4-dihydro-2H-thieno[3,4-b][1,4]dioxepine or 3,3-diallyl-3,4-dihydro-2H-thieno[3,4-b][1,4]dioxepine with a thiol having a hydrocarbyl moiety optionally containing one or more heteroatom-containing functional groups under radical addition conditions under radical addition conditions. Such monomers may be used in homo- or copolymerization processes to obtain thiophene-type polymers containing substituents (which may bear functional groups such as silane, thiol, hydroxyl, carboxylic acid, amine, sugar groups, polyoxyalkylene, and the like). Crosslinkers useful for introducing crosslinking into thiophene-type polymers may be prepared by reacting 3-allyl-3,4-dihydro-2H-thieno[3,4-b][1,4]dioxepine with a compound having two or more thiol groups under radical addition conditions.

23 Claims, 2 Drawing Sheets

SUBSTITUTED 3,4-PROPYLENEDIOXYTHIOPHENE MONOMERS AND 3,4-PROPYLENEDIOXYTHIOPHENE-BASED CROSSLINKERS AND POLYMERS THEREOF

CROSS-REFERENCE TO RELATED APPLICATION

This application claims priority from U.S. Provisional Application No. 61/377,694, filed Aug. 27, 2010, and incorporated herein by reference in its entirety for all purposes.

ACKNOWLEDGEMENT OF FEDERAL FUNDING

This invention was made with support under Contract Number W911NF-06-1-0218, awarded by the Army Research Office; the United States federal government, therefore, has certain rights in the invention.

FIELD OF THE INVENTION

The invention pertains to substituted 3,4-propylenedioxythiophene monomers and 3,4-propylenedioxythiophene-based crosslinkers and polymers prepared therefrom.

BACKGROUND OF THE RELATED ART

Many different polythiophenes have been studied extensively in recent years due to their interesting and useful electrical and/or optical characteristics. For example, polythiophenes generally become electrically conducting upon chemical or electrochemical oxidation or reduction.

However, there remains a need in this field to develop additional types of thiophene monomers and crosslinkers which can be used, by themselves or in copolymers with other monomers, to prepare polythiophenes having varied or improved properties in order to meet certain desired end-use requirements. For example, the introduction of functionalized thiophene monomers bearing one or more substituents which may have functional groups capable of being further reacted or modifying particular attributes of the polymer would be of great interest, since such functional and/or substituted monomers can enhance the versatility of thiophene polymers.

SUMMARY OF THE INVENTION

Electroconductive monomers containing a 3,4-propylenedioxythiophene (ProDOT) moiety and one or two substituents pendant thereto (each of which may bear one or more functional groups) have been prepared by modification of previously known monomers, 3-allyl-3,4-dihydro-2H-thieno[3,4-b][1,4]dioxepine (ProDOT-ene, which contains a —$CH_2CH=CH_2$ group substituted at the middle carbon of the propylene unit in the 3,4-propylenedioxythiophene moiety) and 3,3-diallyl-3,4-dihydro-2H-thieno[3,4-b][1,4]dioxepine (ProDOT-diene, which contains two —$CH_2CH=CH_2$ groups substituted at the middle carbon of the propylene unit in the 3,4-propylenedioxythiophene moiety). These monomers contain side chain pendant double bonds which have been found to be reactive towards a variety of thiols upon thermally or photochemically initiated radical addition. The hydrothiolation reaction may also be accomplished by means of an ionic mechanism. Functional thiols can be utilized to produce substituted ProDOT monomers containing, e.g., carboxylic acid, amine, peptide, silane, thiol, peptide and sugar functional groups. Thiols containing hydrocarbyl groups such as alkyl groups may also be employed to obtain hydrocarbyl-substituted ProDOT monomers. The mono- and di-substituted monomers can be chemically or electrochemically polymerized to yield conductive poly(ProDOT) containing the desired functionality in the side chain(s).

The invention provides a simple and general method for the synthesis of electroactive monomers containing a wide variety of functional and/or hydrocarbyl side chains. Using the methods described herein, a single precursor can be used as a starting point to synthesize a wide range of useful, functional monomers using one-step chemistry.

The ability to create functionalized conjugated polymers is expected to be important for improving interactions with solid substrates, and for tailoring the biological response with living tissue. It may also be possible to create functional, soluble conjugated polymers that could be processed into useful fibers or films. Selecting different substituted monomers for incorporation into a thiophene polymer also permits the phobicity of the polymer to be adjusted as may be desired for a particular end-use application. For example, if the substituent on the monomer is hydrophobic, such as a long chain alkyl group, the resulting polymer derived therefrom will generally be more hydrophobic than a polymer prepared using a monomer bearing a hydrophilic substituent (such as a substituent containing one or more sulfonic acid, polyoxyethylene, hydroxyl, or carboxylic acid functional groups). The solubility of the polymer in various solvents may also be adjusted as may be desired by selection of different substituents/functional groups.

The present invention also provides crosslinkers containing two or more ProDOT-based moieties per molecule that are capable of being chemically or electrochemically polymerized, optionally together with one or more monomers such as ProDOT or EDOT, to yield crosslinked conductive polymers. Such crosslinkers may be prepared by reacting ProDOT-ene with a polythiol-functionalized compound, e.g., a compound containing two or more —SH groups per molecule.

Thus, one aspect of the invention provides a substituted 3,4-propylenedioxythiophene monomer represented by structure ProDOT-[($CH_2$)$_3$—S—R]$_p$, wherein ProDOT is a 3,4-propylenedioxythiophene moiety, p is 1 or 2, and R is a hydrocarbyl moiety optionally containing one or more heteroatom-containing functional groups. When p=2, the R groups may be the same or different.

In another aspect of the invention, R contains one or more heteroatom-containing functional groups selected from silanes, ether, sulfonic acid and salts and esters thereof, thiol, hydroxyl, amines and salts thereof, and carboxylic acid and salts and esters thereof.

In still another aspect of the invention, R is a) —X—R$^1$, wherein X is a divalent hydrocarbyl moiety comprised of two or more carbon atoms and R$^1$ is a silane, sulfonic acid (—SO$_3$H or an ester, or salt thereof), hydroxyl, amine (or amine salt), thiol, peptide or polyoxyalkylene functional group, b) —Y—R$^2$, wherein Y is a divalent hydrocarbyl moiety comprised of one or more carbon atoms and R$^2$ is a carboxylic acid functional group (—CO$_2$H or an ester or salt thereof) or —CHOHCH$_2$OH, or c) —R$^3$, wherein R$^3$ is a sugar moiety or a hydrocarbyl moiety.

Yet another aspect of the invention furnishes a polyfunctional 3,4-propylenedioxythiophene crosslinker represented by structure (ProDOT-(CH$_2$)$_3$—S—)$_o$—Z, wherein ProDOT is a 3,4-propylenedioxythiophene moiety, o is two or more, and Z is a polyvalent organic moiety. In one embodiment, Z is:

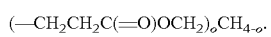

The invention further provides a method of preparing a monomer, comprising contacting 3-allyl-3,4-dihydro-2H-thieno[3,4-b][1,4]dioxepine or 3,3-diallyl-3,4-dihydro-2H-thieno[3,4-b][1,4]dioxepine with a thiol containing a hydrocarbyl group, optionally having one or more functional groups, under radical addition conditions. A mixture of different thiols may be utilized in such a reaction.

Additionally provided by the invention is a method of preparing a crosslinker, comprising contacting 3-allyl-3,4-dihydro-2H-thieno[3,4-b][1,4]dioxepine with a compound having two or more thiol groups under radical addition conditions.

Still another aspect of the invention provides a polymer prepared by polymerization of at least one monomer and/or crosslinker as described above. The polymer may be a homopolymer or copolymer.

DETAILED DESCRIPTION OF THE INVENTION

Substituted 3,4-Propylenedioxythiophene Monomer

Figure 1:
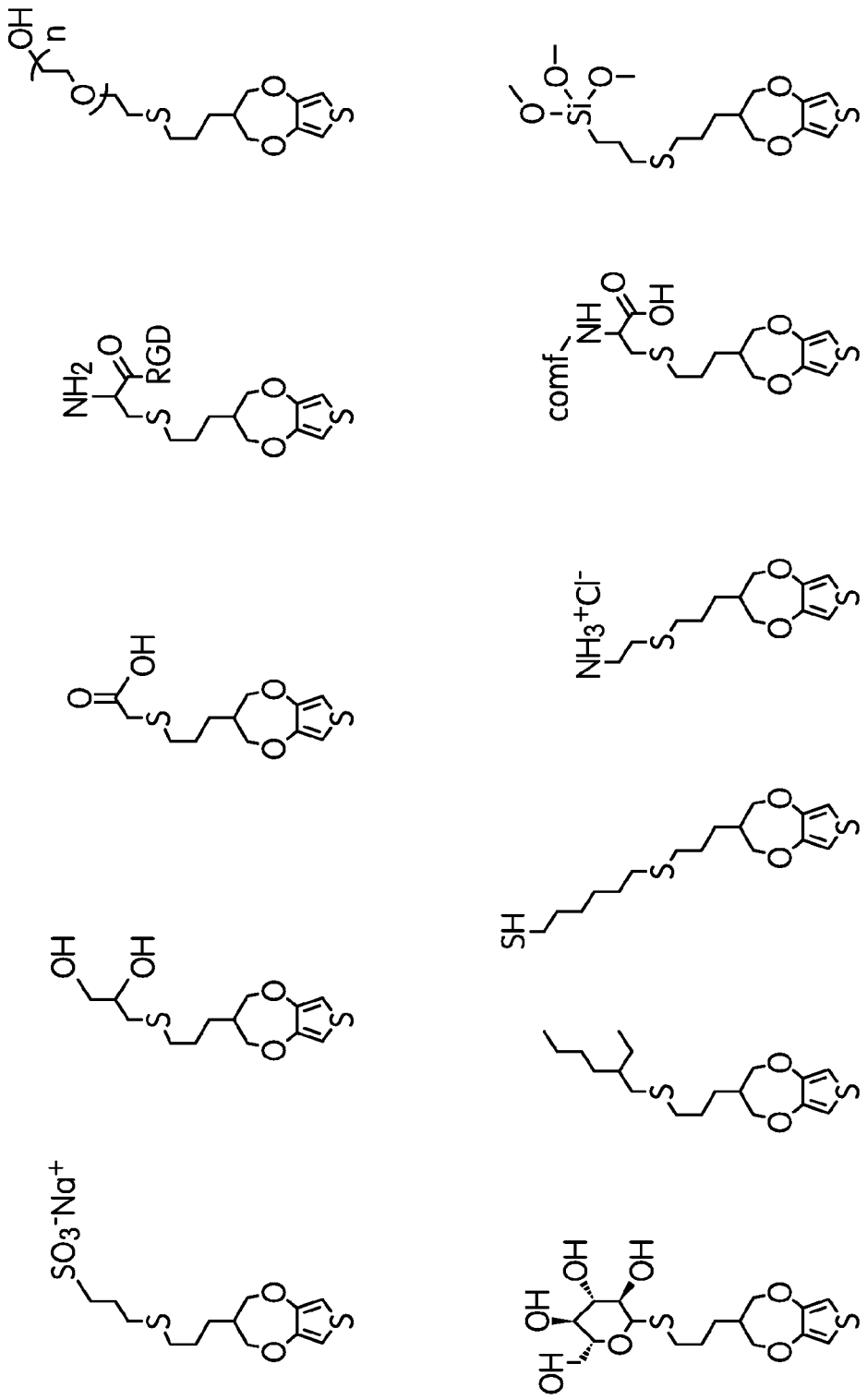
FIG. 1 illustrates various exemplary monomers in accordance with the invention.

The precursor monomers, 3-allyl-3,4-dihydro-2H-thieno[3,4-b][1,4]dioxepine and 3,3-diallyl-3,4-dihydro-2H-thieno[3,4-b][1,4]dioxepine, may be synthesized in two steps from commercially available starting materials in accordance with known, published procedures. See, for example, WO 2006/117800, incorporated herein by reference in its entirety for all purposes. Functionalization of the monomers is achieved by reaction with a thiol (including a mixture of different thiols) containing the desired chemistry, e.g., carboxylic acid, amine, ether, ester, amide nitrile, amino acid, silane, thiol, hydrocarbyl, sulfonic acid, polyoxyalkylene, amide, ketone, sugar or peptide. The thiol adds across the carbon-carbon double bond in a hydrothiolation reaction, which may proceed through a free radical or ionic mechanism. The reaction, illustrated in Scheme 1 where the precursor monomer is 3-allyl-3,4-dihydro-2H-thieno[3,4-b][1,4]dioxepine, can be initiated using either thermal or photochemical radical initiators (e.g., azo compounds, peroxides, ketones such as DMPA, benzophenone and thioxanthone) and is typically complete in one hour or less. For example, the reaction may be promoted by irradiating a mixture of the reactants, together with a free radical initiator such as 2,2-dimethoxy-2-phenylacetophenone (DMPA), with ultraviolet light. The thiol-ene reaction can also be carried out thermally by heating the reactants and, optionally, solvent in the presence of an initiator such as AIBN (which is typically present at a concentration about 0.05 to about 0.2 weight %). Temperatures of about 50° C. to about 70° C. and reaction times of about 2 to about 50 hours will generally be sufficient. The R group in the reactant R—SH is a hydrocarbyl or functionalized hydrocarbyl moiety. Although it is not necessary to conduct the reaction under an inert atmosphere, an inert atmosphere may help to ensure complete reaction when solvent is used. If no solvent is present, the reaction may be carried out under ambient conditions (i.e., in air). Following the reaction, the desired monomer may be isolated and purified if so desired by standard techniques, such as washing, drying, precipitation, recystallization, distillation, extraction, chromatography, and the like.

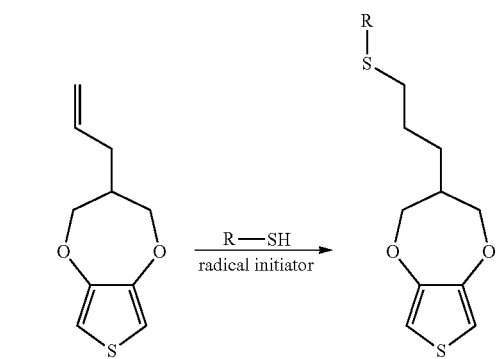

Scheme 1.

A substituted 3,4-propylenedioxythiophene monomer may be represented by structure ProDOT-[$(CH_2)_3$—S—R]$_p$, wherein ProDOT is a 3,4-propylenedioxythiophene moiety, p is 1 or 2, and R is a hydrocarbyl moiety optionally containing one or more heteroatom-containing functional groups. The functional group(s) may be pendant to the hydrocarbyl moiety and/or at the terminus of the hydrocarbyl moiety. Where the precursor monomer is 3-allyl-3,4-dihydro-2H-thieno[3,4-b][1,4]dioxepine, the —$(CH_2)_3$—S—R group is substituted at the 2 (central) position of the bridging propylene moiety of the 3,4-propylenedioxythiophene. Where the precursor monomer is 3,3-diallyl-3,4-dihydro-2H-thieno[3,4-b][1,4]dioxepine, the —$(CH_2)_3$—S—R groups are similarly substituted at the 2 position of the bridging propylene moiety of the 3,4-propylenedioxythiophene. The hydrocarbyl moiety typically contains from one to about 25 carbon atoms, although higher molecular weight monomers are also considered within the scope of the invention. The hydrocarbyl moiety may be completely aliphatic, or completely aromatic, or may contain both aliphatic and aromatic components. Furthermore, the aliphatic portions of the hydrocarbyl moiety may be linear or branched; the moiety may also contain alicyclic components. Preferably, any aliphatic portions of the hydrocarbyl moiety are saturated.

The heteroatom(s) in the optional functional groups(s) may be, for example, sulfur, oxygen, nitrogen, silicon or some combination thereof. The functional group may contain one or more active hydrogens, as may be supplied for example by a carboxylic acid (—$CO_2H$), thiol (—SH), or hydroxyl (—OH) group. Illustrative functional groups include, without limitation, silane groups, ether groups (—O—), sulfonic acid groups (—$SO_3H$) and salts and esters thereof, thiol groups, hydroxyl groups, amine groups (primary, secondary, tertiary) and salts thereof (e.g., ammonium halide salts, alkyl ammonium salts), ketones, amides, amino acids, nitrile, and carboxylic acid groups and salts and esters thereof. In the aforementioned formula, R may be, for example, a) —X—$R^1$, wherein X is a divalent hydrocarbyl moiety comprised of two or more carbon atoms and $R^1$ is a silane, sulfonyl (including —$SO_3H$ and salts and esters thereof), hydroxyl, amine, thiol, peptide or polyoxyalkylene functional group, b) —Y—$R^2$, wherein Y is a divalent hydrocarbyl moiety comprised of one or more carbon atoms and $R^2$ is a carboxylic acid functional group (including —$CO_2H$ and salts and esters thereof) or —$CHOHCH_2OH$, or c) —$R^3$, wherein $R^3$ is a sugar moiety or a hydrocarbyl moiety (containing 2 to 25 carbon atoms, for example). In one embodiment, where R is —X—R$^1$, X is —(CH$_2$)$_m$—, and m is 2 or more (up to 20, or more, for example). In another embodiment of the invention, where R is —Y—R$^2$, Y is —(CH$_2$)$_n$—, and n is 1 or more (up to 21 or more, for example). Specific embodiments include monomers where R is selected from the group consisting of a) —(CH$_2$)$_3$—Si(OR$^4$)$_3$, where R$^4$ is a C$_1$-C$_4$ alkyl group, b) —(CH$_2$)$_3$—SO$_3$H and salts thereof, c) —CH$_2$—CO$_2$H and salts thereof, d) —CH$_2$CH(NH$_2$)C(=O)RGD, e) —CH$_2$CHOHCH$_2$OH, —(CH$_2$)$_2$NH$_2$ and salts thereof, g) —(CH$_2$)$_6$SH, h) —CH$_2$CH$_2$—(OCH$_2$CH$_2$)$_p$—OH, where p is 0 to 100, i) ethylhexyl, and j) glucosyl.

FIG. 1 illustrates various exemplary monomers which may be prepared in accordance with the present invention.

3,4-Propylenedioxythiophene-Based Crosslinker

Crosslinkers in accordance with the invention contain two or more ProDOT moieties per molecule which are capable of reacting, typically with thiophene-type monomers, to form crosslinked polymers. The ProDOT moieties are bonded to a polyvalent organic moiety, which acts as a crosslinking site when the crosslinker is incorporated into a polymer. The precursor monomer, 3-allyl-3,4-dihydro-2H-thieno[3,4-b][1,4]dioxepine, may be contacted with a compound having two or more thiol groups under radical addition conditions. Typically, the stoichiometry of the reactants is adjusted such that there is a sufficient amount of the precursor monomer to react with all the available thiol groups of the thiol-containing compound.

The reaction, illustrated in Scheme 2, can be initiated using either thermal or photochemical radical initiators (e.g., azo compounds, peroxides, ketones such as DMPA, benzophenone and thioxanthone) and is typically complete in one hour or less. For example, the reaction may be promoted by irradiating a mixture of the reactants, together with a free radical initiator such as 2,2-dimethoxy-2-phenylacetophenone (DMPA), with ultraviolet light. The thiol-end reaction can also be carried out thermally by heating the reactants and, optionally, solvent in the presence of an initiator such as AIBN (which is typically used at a concentration about 0.05 to about 0.2 weight %). Temperatures of about 50° C. to about 70° C. and reaction times of about 2 to about 50 hours will generally be sufficient. Although it is not necessary to conduct the reaction under an inert atmosphere, an inert atmosphere may help to ensure complete reaction when solvent is used. If no solvent is present, the reaction may be carried out under ambient conditions (i.e., in air). Following the reaction, the desired crosslinker may be isolated and purified if so desired by standard techniques such as precipitation, recrystallization, distillation, chromatography, washing, drying, extraction and the like.

Scheme 2.

o is an integer of 2 or greater and Z is a polyvalent organic moiety

The crosslinker may be represented by structure (ProDOT-(CH$_2$)$_3$—S—)$_o$—Z, wherein ProDOT is a 3,4-propylenedioxythiophene moiety, o is two or more (e.g., 2 to 6), and Z is a polyvalent organic moiety. Z may be a polyvalent hydrocarbyl group, but may contain one or more heteroatoms such as oxygen or silicon in addition to carbon and hydrogen. For example, Z may contain one or more ester groups. In one embodiment of the invention, Z is

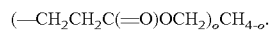

Figure 2:
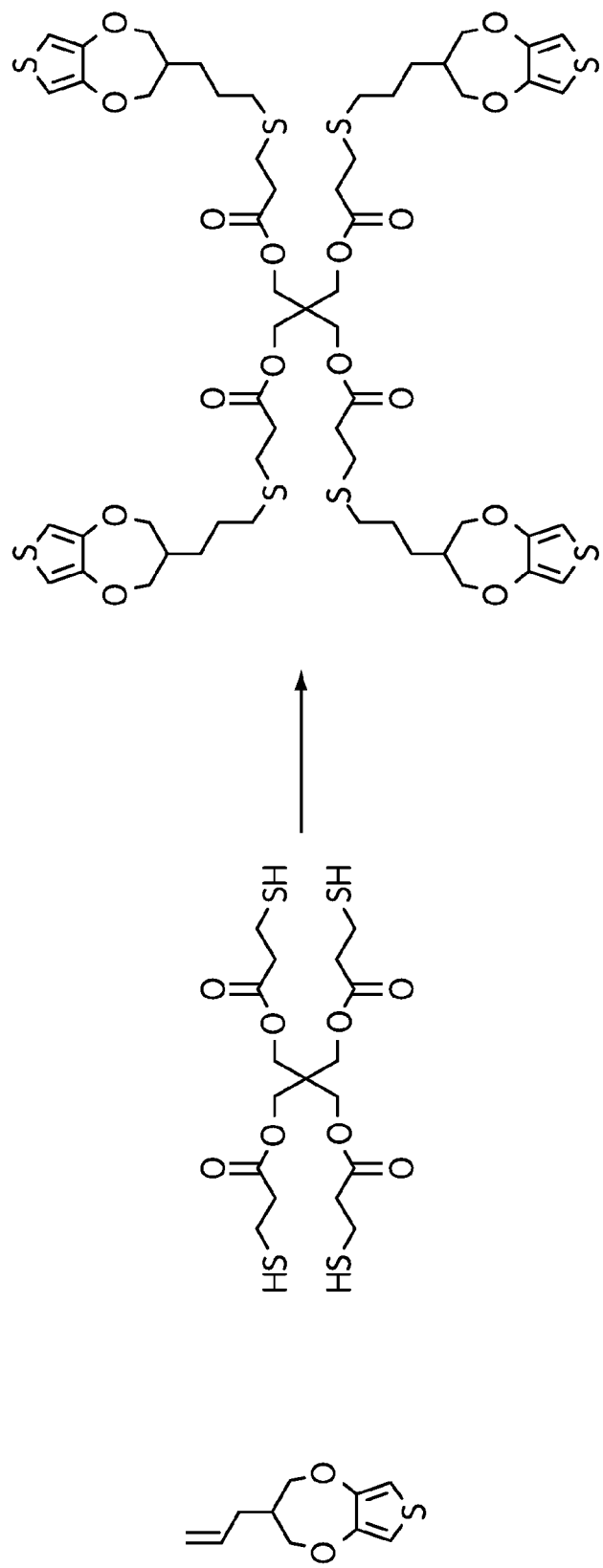
FIG. 2 illustrates a synthetic scheme which can be used to prepare an exemplary crosslinker in accordance with the invention.

In this embodiment, the compound having two or more thiol groups which is reacted with the precursor monomer 3-allyl-3,4-dihydro-2H-thieno[3,4-b][1,4]dioxepine is represented by structure (HS—CH$_2$CH$_2$C(=O)OCH$_2$)$_o$CH$_{4-o}$. FIG. 2 illustrates this reaction.

Other types of compounds containing a plurality of thiol groups which could be reacted with ProDOT-ene to provide crosslinkers in accordance with the invention include, but are not limited to, poly[mercaptopropyl)methylsiloxanes], multi-arm polyethylene glycol thiols (e.g., branched polyethylene glycols in which the terminal hydroxyl groups have been converted to thiol groups), trimethylolpropane tris(3-mercaptopropionate), tris[2-(3-mercaptopropionyloxy)ethyl]isocyanurate, and alkylene dithiols such as 1,6-hexanedithiol.

Polymerization Process

The present invention provides a process for preparing a polymer containing one or more units derived from a substituted 3,4-propylenedioxythiophene monomer represented by structure ProDOT-[(CH$_2$)$_3$—S—R]$_p$, wherein ProDOT is a 3,4-propylenedioxythiophene moiety, p is 1 or 2, and R is a hydrocarbyl moiety optionally containing one or more heteroatom-containing functional groups and/or one or more crosslinking sites derived from a crosslinker represented by structure (ProDOT-(CH$_2$)$_3$—S—)$_o$—Z, wherein ProDOT is a 3,4-propylenedioxythiophene moiety, o is two or more, and Z is a polyvalent organic moiety. The resulting polymer may contain substituents (optionally including functional groups) derived from the substituted 3,4-propylenedioxythiophene monomer which are pendant to a polythiophene backbone and/or crosslinking sites derived from the crosslinker (wherein the 3,4-propylenedioxythiophene moieties become incorporated into polythiophene backbones, possibly from otherwise separate polythiophene chains).

According to one embodiment of the process according to the present invention, the polymerization process is a chemical or an electrochemical process. Homopolymers as well as copolymers may be prepared. For example, a substituted 3,4-propylenedioxythiophene monomer in accordance with the invention may be homopolymerized. Mixtures of two or more different substituted 3,4-propylenedioxythiophene monomers in accordance with the invention may be copolymerized. The present invention also includes the copolymerization of one or more substituted 3,4-propylenedioxythiophene monomers as disclosed herein with one or more other types of monomers, such as other thiophenes such as ProDOT, EDOT or ProDOT-ene or non-thiophene comonomers such as pyrroles. The relative proportions of substituted 3,4-propylenedioxythiophene monomer and other types of monomers may be selected in accordance with the degree of substitution and/or functionalization contributed by the 3,4-propylenedioxythiophene monomer which is desired in the polymer. A crosslinker in accordance with the invention may be homopolymerized, but more typically is employed as a crosslinking agent in a copolymerization process with one or more monomers, such as one or more substituted 3,4-propylenedioxythiophene monomers as disclosed herein and/or one or more other types of monomers, such as other thiophenes such as ProDOT, EDOT, ProDOT-ene, ProDOT-diene or non-thiophene comonomers. The amount of crosslinker relative to other monomers may be varied as many be desired to provide polymers having different degrees of crosslink density.

Chemical Polymerization

Chemical polymerization, according to the present invention, can be carried out oxidatively or reductively. The oxidation agents used for the oxidative polymerization of pyrrole, such as described for example in Journal of the American Chemical Society, volume 85, pages 454-458 (1963) and J. Polymer Science Part A Polymer Chemistry, volume 26, pages 1287-1294 (1988), can be utilized for the oxidative polymerization of thiophenes and may be adapted for use with the monomers and crosslinkers of the present invention.

According to one embodiment of the polymerization process according to the present invention, the process is a chemical process in which inexpensive and easily accessible oxidizing agents such as iron(III) salts such as $FeCl_3$ (ferric chloride), the iron(III) salts of organic acids, e.g. $Fe(OTs)_3$, $H_2O_2$, $K_2Cr_2O_7$, alkali and ammonium persulphates, copper perchlorate, iron perchlorate, alkali perborates and potassium permanganate are used therein to initiate the polymerization.

Theoretically, the oxidative polymerization of thiophenes requires 2.25 equivalents of oxidizing agent per mole of thiophene [see e.g. J. Polymer Science Part A Polymer Chemistry, volume 26, pages 1287-1294 (1988)]. In practice, an excess of 0.1 to 2 equivalents of oxidation agent is typically used per polymerizable unit. The use of persulphates and iron(III) salts has the great technical advantage that they do not act corrosively. Oxidative polymerization can be accelerated by heating the monomer(s), for example, after placing a coating of the monomer(s) on a substrate surface.

Reductive polymerization can be performed using any of the conventional reductive polymerization techniques known in the thiophene art, such as the Stille (organotin) or Suzuki (organoboron) routes or with nickel complexes.

Electrochemical Polymerization

Substituted 3,4-propylenedioxythiophene monomers and 3,4-propylenedioxythiophene crosslinkers as disclosed herein also can be polymerized electrochemically. Electrochemical oxidative polymerization of such monomers and crosslinkers may be carried out at any temperature effective to permit the polymerization to proceed at a practicably rapid rate. Typically, temperatures between about −20° C. and 60° C. are suitable. The reaction time, depending upon the particular monomer or crosslinker or mixture of monomers, is generally between a few seconds and several hours. Electrochemical polymerization of thiophene compounds was described in 1994 by Dietrich et al. in Journal Electroanalytical Chemistry, volume 369, pages 87-92. In a typical electrochemical polymerization, a potential is applied across a solution containing a thiophene-type monomer and an electrolyte, producing a polymeric film on the anode. Oxidation of the monomer produces a radical cation, which can then couple with a second radical cation to form a dication dimer, or with another monomer to produce a radical cation dimer. Growth of the polymer chain takes place by a series of such coupling reactions.

Inert liquids suitable for use during electrochemical oxidation and polymerization of the monomers and crosslinkers of the present invention include, but are not limited to: water, alcohols such as methanol and ethanol, ketones such as acetophenone, halogenated hydrocarbons such as methylene chloride, chloroform, tetrachloromethane and fluorohydrocarbons; esters such as ethyl acetate and butyl acetate, aromatic hydrocarbons such as benzene, toluene and xylene, aliphatic hydrocarbons such as pentane, hexane, heptane and cyclohexane, nitriles such as acetonitrile and benzonitrile, sulfoxides such as dimethylsulfoxide, sulfones such as dimethylsulfone, phenylmethylsulfone and sulfolan, liquid aliphatic amides such as methyl acetamide, dimethyl acetamide, dimethyl formamide, pyrrolidone, N-methyl-pyrrolidone, caprolactam, N-methyl-caprolactam, aliphatic and mixed aliphatic and aromatic ethers such as diethylether and anisole, liquid ureas such as tetramethylurea or N,N-dimethyl-imidazolidinone.

Electrolyte additives for use in the electrochemical polymerization of the monomers and crosslinkers of the invention are preferably free acids or the usual conducting salts, which exhibit a certain solubility in the solvent used. Particularly suitable electrolytes are alkali, alkaline earth or optionally alkylated ammonium, phosphonium, sulfonium or oxonium cations in combination with perchlorate, tosylate, tetrafluoroborate or hexafluorophosphonate anions. The electrolyte additives may be used in such quantities that a current of at least 0.1 mA flows during electrochemical oxidation.

Electrochemical polymerization can be carried out continuously or discontinuously. Known electrode materials are ITO-covered glass, precious metal or steel mesh, carbon-filled polymers, evaporated metal-coated insulator layers and carbon felt.

Current densities during electrochemical oxidation may vary within wide limits. According to one embodiment of the present invention, the current density is 0.0001 to 100 $mA/cm^2$. According to another embodiment of the process according to the present invention, the current density is 0.01 to 40 $mA/cm^2$. At such current densities, voltages of ca. 0.1 to 50 V are typically set up.

Chemically or electrochemically prepared polymers derived from monomers and crosslinkers in accordance with the invention exhibit high electrical conductivity together with low absorption of visible light and high absorption to infrared radiation. Therefore layers thereof are highly electrically conducting, highly transparent to visible light and heat shielding. Such polymers can be applied by a wide variety of techniques including printing techniques in which the polymer is applied, for example, as an ink or paste using standard techniques, the properties of the paste or ink being adapted to the particular printing technique by adding one of more of organic solvents, binders, surfactants and humectants, to a wide variety of rigid and flexible substrates, e.g. ceramics, glass and plastics, and are particularly suitable for flexible substrates such as plastic sheeting and the substrates can be substantially bent and deformed without the polythiophene layer losing its electrical conductivity. Such polymers especially lend themselves to the production of electroconductive patterns.

The thiophene-based polymers of the present invention can therefore be utilized, for example, in electrochromic devices, photovoltaic devices, batteries, diodes, capacitors and organic and inorganic electroluminescent devices, in electromagnetic shielding layers, in heat shielding layers, in antistatic coatings for a wide variety of products including photographic film, thermographic recording materials and photothermographic recording materials, in smart windows, in sensors for organic and bio-organic materials (e.g., chemical sensors), in field effect transistors, in printing plates, in conductive resin adhesives, in solar cells, in photochemical resists, in nonlinear optic devices and in free-standing electrically conductive films.

Applications for polymers in accordance with the invention include both static applications, which rely upon the intrinsic conductivity of the polymer combined with its ease of processing and material properties as a polymeric material, and dynamic applications, which utilize changes in the conductive and/or optical properties of the polymer resulting either from application of electric potentials or from environmental stimuli.

Polymers in accordance with the invention may be doped, in order to modify their conductivity and other properties. Suitable dopants may include, for example, halogens such as iodine and bromine, organic acids such as trifluoroacetic acid, propionic acid, and sulfonic acids, ferric chloride, and the like.

EXAMPLES

A number of exemplary substituted ProDOT monomers and crosslinkers in accordance with the present invention were prepared using the following synthetic procedures.

General procedures and materials: Sodium 3-mercapto-1-propanesulfonate was purchased from TCI America. Thioglycolic acid was purchased from Alfa Aesar. Thioglycerol, 1-thio-β-D-glucose sodium salt, and 2-ethylhexanethiol were purchased from Sigma Aldrich. All other reagents and solvents were purchased from Fisher Scientific and used as received. Samples were irradiated using a UVP Black Ray UV Bench Lamp XX-15L, emitting 365 nm light at 15 W. NMR spectra ($^1$H and $^{13}$C) were acquired on a Bruker DRX-400 spectrometer at room temperature. Chemical shifts are reported in parts per million, referenced to the solvent as internal standard (CHCl$_3$: 7.24 ppm for $^1$H and 77.2 for $^{13}$C; DMSO: 2.50 for $^1$H and 77.2 ppm for $^{13}$C). FTIR spectra were collected on a Perkin Elmer Spectrum 100 spectrometer fitted with the Universal ATR accessory.

Synthesis of ProDOT-(CH$_2$)$_3$—S—CH$_2$CO$_2$H. ProDOT-ene (100 mg, 0.51 mmol) and thioglycolic acid (70 mg, 0.76 mmol) were added to a vial along with 0.1 wt % of 2,2-dimethoxy-2-phenylacetophenone (DMPA). The mixture was vortexed to ensure thorough mixing and dissolution of the initiator. The vial was placed under a UV lamp and irradiated for one hour. A small amount of methanol was added, and the product precipitated using water. The supernatant was decanted and the product redissolved in ethyl acetate, dried with MgSO$_4$, and concentrated by evaporation to give a viscous oil (114 mg, 78%). $^1$H NMR (400 MHz, CDCl$_3$): δ=6.49 (s, 2H), 4.12 (dd, 2H), 3.92 (dd, 2H), 3.27 (s, 2H), 2.71 (t, 2H), 2.16 (m, 1H), 1.73 (m, 2H), 1.57 ppm (m, 2H). $^{13}$C NMR: δ=175.8, 149.9, 105.8, 74.2, 42.1, 33.4, 32.7, 26.8, 26.3 ppm. FTIR: 3109, 2921, 2864, 1704, 1560, 1482, 1451, 1375, 1295, 1188, 1130, 1005, 850, 775 cm$^{-1}$.

Synthesis of ProDOT-(CH$_2$)$_3$—S—(CH$_2$)$_2$NH$_2$. Cysteamine HCl (86 mg, 0.76 mmol) and a minimum of methanol were added to a vial and heated to dissolve the thiol. ProDOT-ene (100 mg, 0.51 mmol) and 0.1 wt % of 2,2-dimethoxy-2-phenylacetophenone (DMPA) were added, and the mixture sparged with argon for five minutes. The vial was placed under a UV lamp and irradiated for one hour. Diethyl ether was added to precipitate the product, which was filtered and dried under vacuum. The dried product was dissolved in water (2 mL) and 10%.NaOH was added to neutralize the ammonium side chains. The aqueous phase was extracted using ethyl acetate (3×5 mL). The combined organic phases were dried with MgSO$_4$ and concentrated by evaporation to give a viscous oil (121 mg, 87%). $^1$H NMR (400 MHz, CDCl$_3$): δ=6.48 (s, 2H), 4.11 (dd, 2H), 3.90 (dd, 2H), 2.88 (br, 2H), 2.63 (t, 2H), 2.54 (t, 2H), 2.15 (m, 1H), 1.82 (br, 2H), 1.68 (m, 2H), 1.55 (m, 2H). $^{13}$C NMR: δ=149.9, 105.7, 74.3, 42.1, 40.9, 36.1, 31.7, 27.1, 27.0 ppm. FTIR: 3104, 2921, 2858, 1561, 1484, 1454, 1377, 1192, 1013, 854, 780 cm$^{-1}$.

Synthesis of ProDOT-(CH$_2$)$_3$—S—(CH$_2$)$_3$SO$_3$Na. Sodium 3-mercapto-1-propanesulfonate (120 mg, 0.68 mmol) and a minimum of methanol were added to a vial and heated to dissolve the thiol. ProDOT-ene (200 mg, 1.02 mmol) and 0.1 wt % of 2,2-dimethoxy-2-phenylacetophenone (DMPA) were added, and the mixture sparged with argon for five minutes. The vial was placed under a UV lamp and irradiated for one hour. Diethyl ether was added to precipitate the product, which was filtered and dried under vacuum to give a white powder (230 mg, 91%). $^1$H NMR (400 MHz, CD$_3$OD): δ=6.52 (s, 2H), 4.08 (dd, 2H), 3.87 (dd, 2H), 2.92 (m, 2H), 2.66 (t, 2H), 2.57 (t, 2H), 2.13 (m, 1H), 2.05 (m, 2H), 1.70 (m, 2H), 1.55 (m, 2H). $^{13}$C NMR: δ=150.3, 105.3, 74.4, 50.0, 42.2, 31.1, 30.2, 26.6, 26.5, 24.8 ppm. FTIR: 3451, 3107, 2924, 2862, 1732, 1640, 1560, 1484, 1452, 1376, 1184, 1049, 1008, 853, 776, 737 cm$^{-1}$.

Synthesis of ProDOT—(CH$_2$)$_3$—S—CH$_2$CH(OH)CH$_2$OH. ProDOT-ene (100 mg, 0.51 mmol) and thioglycerol (83 mg, 0.76 mmol) were added to a vial along with 0.1 wt % of 2,2-dimethoxy-2-phenylacetophenone (DMPA). A minimum of methanol was added to dissolve the reactants and the mixture sparged with argon for five minutes. The vial was placed under a UV lamp and irradiated for one hour. The product was then precipitated using water. The supernatant was decanted and the product redissolved in ethyl acetate, dried with MgSO$_4$, and concentrated by evaporation to give a viscous oil (100 mg, 65%). $^1$H NMR (400 MHz, CDCl$_3$): δ=6.49 (s, 2H), 4.11 (dd, 2H), 3.92 (dd, 2H), 3.81 (m, 1H), 3.76 (dd, 1H), 3.57 (dd, 1H), 2.72 (dd, 1H), 2.63 (d, 1H), 2.58 (t, 2H), 2.54 (br, 2H), 2.15 (m, 1H), 1.70 (m, 2H), 1.55 (m, 2H). $^{13}$C NMR: b=149.9, 105.8, 74.2, 69.9, 65.3, 42.1, 35.7, 32.3, 27.0, 26.9 ppm. FTIR: 3383, 3107, 2917, 2865, 1559, 1483, 1452, 1375, 1190, 1007, 851, 776 cm$^{-1}$.

Synthesis of ProDOT-(CH$_2$)$_3$—S—CH$_2$CH(CH$_2$CH$_3$)CH$_2$CH$_2$CH$_2$CH$_3$. ProDOT-ene (250 mg, 1.28 mmol) and 2-ethylhexanethiol (330 μL, 1.90 mmol) were added to a vial along with 0.1 wt % of 2,2-dimethoxy-2-phenylacetophenone (DMPA). The mixture was vortexed to ensure thorough mixing and dissolution of the initiator. The vial was placed under a UV lamp and irradiated for one hour. The product was purified by column chromatography, eluting with 10% ethyl acetate/90% hexanes, to give a clear oil (325 mg, 74%). $^1$H NMR (400 MHz, CDCl$_3$): δ=6.49 (s, 2H), 4.13 (dd, 2H), 3.90 (dd, 2H), 2.51 (q, 4H), 2.17 (m, 1H), 1.68 (m, 2H), 1.60-1.20 (m, 11H), 0.91 (t, 3H), 0.88 (t, 3H). $^{13}$C NMR: b=150.0, 105.7, 74.4, 42.2, 39.3, 36.8, 32.8, 32.4, 28.9, 27.1, 25.5, 23.0, 14.1, 10.8 ppm. FTIR: 3108, 2957, 2924, 2858, 1560, 1484, 1454, 1375, 1190, 1043, 1012, 851, 773 cm$^{-1}$.

Synthesis of ProDOT-(CH$_2$)$_3$—S—(CH$_2$)$_3$—Si(OCH$_3$)$_3$. ProDOT-ene (50 mg, 0.256 mmol) and 3-mercaptopropyltrimethoxysilane (57 μL, 0.38 mmol) were added to a vial along with 0.1 wt % of 2,2-dimethoxy-2-phenylacetophenone (DMPA). The mixture was vortexed to ensure thorough mixing and dissolution of the initiator. The vial was placed under a UV lamp and irradiated for one hour. The product was not purified. $^1$H NMR (400 MHz, CDCl$_3$): δ=6.45 (s, 2H), 4.10 (dd, 2H), 3.86 (dd, 2H), 3.60 (s, 9H), 2.50 (t, 4H), 2.14 (m, 1H), 1.64 (m, 4H), 1.52 (m, 2H), 0.73 (m, 2H).

Synthesis of ProDOT-(CH$_2$)$_3$—S-glucose. ProDOT-ene (10 mg, 0.051 mmol), 1-thio-β-D-glucose sodium salt (17 mg, 0.076 mmol), and concentrated HCl (6.32 μL, 0.076 mmol) were dissolved in DMF and added to a vial along with 0.1 wt % of 2,2-dimethoxy-2-phenylacetophenone (DMPA). The mixture was vortexed to ensure thorough mixing and dissolution of the initiator. The vial was placed under a UV lamp and irradiated for one hour. Water was added, and the aqueous layer extracted with ethyl acetate. The organic fraction was dried with MgSO$_4$, filtered, and the solvent evaporated to give a clear oil. $^1$H NMR (400 MHz, CDCl$_3$): δ=6.48 (s, 2H), 5.06 (br, 4H), 4.45 (br, 1H), 4.06 (br, 2H), 3.86 (br, 4H), 3.62 (br, 2H), 3.40 (br, 2H), 2.71 (br, 2H), 2.10 (br, 1H), 1.70 (br, 2H), 1.54 (br, 2H). FTIR: 3383, 3107, 2917, 2865, 1541, 1484, 1453, 1376, 1261, 1191, 1016, 796 cm$^{-1}$.

ProDOT-($CH_2$)$_3$—S—($CH_2$)$_6$—SH. 30 mg of ProDOT-ene, 70 mg of hexanedithiol, and 2 mg of dimethoxyphenylacetophenone were vortexed until homogeneous. The mixture was irradiated using a 365 nm UV lamp for one hour. The product was precipitated using methanol. An NMR spectrum of the product was consistent with the structure ProDOT-($CH_2$)$_3$—S—($CH_2$)$_6$—SH.

Electropolymerization procedure using substituted monomers. Polymer films were electrochemically deposited using an Autolab PGstat12 Potentiostat/Galvanostat (EcoChemie) at 0.5 mA/cm$^2$ using a three electrode cell. Gold coated silicon wafers (Platypus Technologies) served as the working electrodes and a platinum wire as the counter electrode, with a Ag/Ag$^+$ wire as the pseudoreference electrode. Deposition solutions consisted of monomer (50 mM) and tetrabutylammonium perchlorate (TBAP, 100 mM) dissolved in propylene carbonate. Although stable films could not be formed from solutions of pure functional monomer under these conditions, up to 25 mol % (12.5 mM) of acid-, amine-, glycerol-, or sulfonate-functionalized monomer could be co-deposited with ProDOT. The resulting films showed FTIR spectra consistent with successful incorporation of the functional monomers into the films.

Chemical Polymerization of ProDOT-($CH_2$)$_3$—S—($CH_2$)$_3$SO$_3$Na. FeCl$_3$ (165 mg, 1 mmol) was suspended in 5 mL of CHCl$_3$. A solution of ProDOT-($CH_2$)$_3$—S—($CH_2$)$_3$SO$_3$Na (100 mg, 0.29 mmol) suspended in 10 mL of CHCl$_3$ was added dropwise. After stirring for 18 hours at room temperature, excess methanol was added to precipitate the polymer and wash away any remaining FeCl$_3$. The resulting dark solid was dissolved in 1M NaOH and stirred for two days to exchange iron counterions for sodium. Excess methanol was added to precipitate the polymer, and it was then redissolved in deionized water and dialyzed for two days against deionized water using a 1000 g/mol cutoff membrane. The resulting solution was freeze-dried to give 68 mg (68% yield) of a brown powder.

Chemical Polymerization of ProDOT-($CH_2$)$_3$—S—$CH_2$CH($CH_2CH_3$)$CH_2CH_2CH_2CH_3$. FeCl$_3$ (142 mg, 0.87 mmol) was suspended in 2 mL of CHCl$_3$ with stirring. A solution of ProDOT-($CH_2$)$_3$—S—$CH_2$CH($CH_2CH_3$)$CH_2CH_2CH_2CH_3$ (100 mg, 0.29 mmol) dissolved in 1 mL of CHCl$_3$ was added dropwise, upon which the solution immediately turned dark red. After stirring for 18 hours at room temperature, excess methanol was added to precipitate the polymer and wash away any remaining FeCl$_3$. The resulting solid was filtered and washed with methanol, then dried under vacuum to give 85 mg (85% yield) of a purple powder.

(ProDOT-($CH_2$)$_3$—S—$CH_2CH_2$C(=O)—O—$CH_2$—)$_4$C Crosslinker. 250 mg of ProDOT-ene, 100 mg of pentaerythritol tetrakis(3-mercaptopropionate), and 2 mg of dimethoxyphenylacetophenone were vortexed until homogeneous. The mixture was irradiated using a 365 nm UV lamp for one hour. The product was dissolved in a minimum of ethyl acetate and precipitated using hexanes. An NMR spectrum of the product was consistent with the structure ProDOT-($CH_2$)$_3$—S—$CH_2CH_2$C(=O)—O—$CH_2$—)$_4$C Electropolymerization Procedure Using Crosslinker:

3,4-Ethylenedioxythiophene (EDOT) or ProDOT-ene was dissolved at 50 mM in acetonitrile along with 100 mM of tetrabutylammonium perchlorate and 10 wt % or 25 wt % (relative to EDOT) (ProDOT-($CH_2$)$_3$—S—$CH_2CH_2$C(=O)—O—$CH_2$—)$_4$C crosslinker. The solution was sparged with argon for five minutes before depositions. Polymerization was accomplished by partially immersing an indium tin oxide (ITO) coated glass slide into the solution and applying a current of 5×10$^{-5}$ A for ten minutes, with a platinum wire serving as the counter electrode. Successful polymerization was indicated by the formation of a purple colored film on the ITO characteristic of an electrodeposited poly(3,4-ethylenedioxythiophene), "PEDOT".

What is claimed is:

1. A substituted 3,4-propylenedioxythiophene monomer represented by structure ProDOT-[($CH_2$)$_3$—S—R]$_p$, wherein ProDOT is a 3,4-propylenedioxythiophene moiety, R is a hydrocarbyl moiety optionally containing one or more heteroatom-containing functional groups, and p is 1 or 2.

2. A monomer in accordance with claim 1, wherein R contains one or more heteroatom-containing functional groups selected from silanes, ether, sulfonic acid and salts and esters thereof, thiol, hydroxyl, amines and salts thereof, amides, ketone, nitrile and carboxylic acid and salts and esters thereof.

3. A monomer in accordance with claim 1, wherein R is a) —X—R$^1$, wherein X is a divalent hydrocarbyl moiety comprised of two or more carbon atoms and R$^1$ is a silane, sulfonyl, hydroxyl, amine, thiol, peptide or polyoxyalkylene functional group, b) —Y—R$^2$, wherein Y is a divalent hydrocarbyl moiety comprised of one or more carbon atoms and R$^2$ is a carboxylic acid functional group or —CHOHCH$_2$OH, or c) —R$^3$, wherein R$^3$ is a sugar moiety or a hydrocarbyl moiety.

4. A monomer in accordance with claim 1, wherein R is —X—R$^1$, X is —($CH_2$)$_m$—, and m is 2 or more.

5. A monomer in accordance with claim 1, wherein R is —Y—R$^2$, Y is —($CH_2$)$_n$—, and n is 1 or more.

6. A monomer in accordance with claim 1, wherein R is selected from the group consisting of a) —($CH_2$)$_3$—Si(OR$^4$)$_3$, where R$^4$ is a C$_1$-C$_4$ alkyl group, b) —($CH_2$)$_3$—SO$_3$H and salts thereof, c) —$CH_2$—CO$_2$H and salts thereof, d) —$CH_2CH(NH_2)$C(=O)RGD, e) —$CH_2$CHOHCH$_2$OH, f) —($CH_2$)$_2NH_2$ and salts thereof, g) —($CH_2$)$_6$SH, h) —$CH_2CH_2$—(O$CH_2CH_2$)$_p$—OH, where p is 0 to 100, i) ethylhexyl, and j) glucosyl.

7. A crosslinker represented by structure (ProDOT-($CH_2$)$_3$—S—)$_o$—Z, wherein ProDOT is a 3,4-propylenedioxythiophene moiety, o is two or more, and Z is a polyvalent organic moiety.

8. A crosslinker in accordance with claim 7, wherein Z is (—$CH_2CH_2$C(=O)O$CH_2$)$_o$CH$_{4-o}$.

9. A method of preparing a monomer in accordance with claim 1, comprising contacting 3-allyl-3,4-dihydro-2H-thieno[3,4-b][1,4]dioxepine or 3,3-diallyl-3,4-dihydro-2H-thieno[3,4-b][1,4]dioxepine with a thiol having a hydrocarbyl moiety optionally containing one or more heteroatom-containing functional groups under radical addition conditions.

10. A method of preparing a crosslinker in accordance with claim 7, comprising contacting 3-allyl-3,4-dihydro-2H-thieno[3,4-b][1,4]dioxepine with a compound having two or more thiol groups under radical addition conditions.

11. A method in accordance with claim 10, wherein the compound having two or more thiol groups is represented by structure (HS—$CH_2CH_2$C(=O)O$CH_2$)$_o$CH$_{4-o}$.

12. A polymer prepared by polymerization of at least one monomer in accordance with claim 1.

13. A polymer in accordance with claim 12, wherein the polymer is prepared by copolymerization of at least one monomer in accordance with claim 1 and at least one additional monomer.

14. A polymer in accordance with claim 13, wherein the at least one additional monomer includes at least one of 3,4- propylenedioxythiophene (ProDOT), 3,4-ethylenedioxythiophene (EDOT), or 3-allyl-3,4-dihydro-2H-thieno[3,4-b][1,4]dioxepine.

15. A polymer prepared by polymerization of a crosslinker in accordance with claim 7.

16. A polymer, wherein the polymer is prepared by copolymerization of at least one crosslinker in accordance with claim 7 and at least one additional monomer.

17. A polymer in accordance with claim 16, wherein the at least one additional monomer includes at least one of 3,4-propylenedioxythiophene (ProDOT), 3,4-ethylenedioxythiophene (EDOT), or 3-allyl-3,4-dihydro-2H-thieno[3,4-b][1,4]dioxepine.

18. A method of making a polymer, the method comprising polymerizing by electropolymerization at least one monomer in accordance with claim 1.

19. A method in accordance with claim 18, wherein the at least one monomer in accordance with claim 1 is copolymerized with at least one additional monomer.

20. A method in accordance with claim 19, wherein the at least one additional monomer includes at least one of 3,4-propylenedioxythiophene (proDOT), 3,4-ethylenedioxythiophene (EDOT), or 3-allyl-3,4-dihydro-2H-thieno[3,4-b][1,4]dioxepine.

21. A method of making a polymer, the method comprising polymerizing by electropolymerization at least one crosslinker in accordance with claim 7.

22. A method in accordance with claim 21, wherein the at least one crosslinker in accordance with claim 7 is copolymerized with at least one additional monomer.

23. A method in accordance with claim 22, wherein the at least one additional monomer includes at least one of 3,4-propylenedioxythiophene (proDOT), 3,4-ethylenedioxythiophene (EDOT), or 3-allyl-3,4-dihydro-2H-thieno[3,4-b][1,4]dioxepine.

* * * * *